United States Patent [19]

Goodman

[11] Patent Number: 4,910,336

[45] Date of Patent: Mar. 20, 1990

[54] PROCESS FOR SEPARATING PHENYLALANINE FROM SALTS

[75] Inventor: Walter H. Goodman, Villa Park, Ill.

[73] Assignee: UOP, Des Plaines, Ill.

[21] Appl. No.: 275,853

[22] Filed: Nov. 25, 1988

[51] Int. Cl.⁴ ............................................. C07C 99/12
[52] U.S. Cl. ..................................................... 562/443
[58] Field of Search ................................. 562/443, 444

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,130,007 | 4/1964 | Breck | 23/113 |
| 3,265,750 | 8/1966 | Peck et al. | 360/666 |
| 3,422,848 | 1/1969 | Liebman et al. | 137/625.15 |
| 3,706,812 | 12/1972 | de Rosset et al. | 260/674 SA |
| 3,787,317 | 1/1974 | Jaworek | 210/31 C |
| 4,024,331 | 5/1977 | Neuzil et al. | 536/1 |
| 4,584,399 | 4/1986 | Portal et al. | 562/443 |
| 4,584,400 | 4/1986 | Otani et al. | 562/443 |
| 4,604,483 | 8/1986 | Kitsukawa et al. | 562/443 |
| 4,642,397 | 2/1987 | Zinnen et al. | 568/934 |
| 4,661,629 | 4/1987 | Valus et al. | 562/443 |
| 4,740,615 | 4/1988 | McManus et al. | 562/443 |

*Primary Examiner*—James H. Reamer
*Attorney, Agent, or Firm*—Thomas K. McBride; John F. Spears, Jr.; Jack H. Hall

[57] ABSTRACT

A process for the liquid phase adsorptive separation of phenylalanine from a fermentation broth feed containing phenylalanine and salts. The feed is contacted with a Y zeolite adsorbent, exchanged with sodium, potassium or calcium ions, to selectively adsorb the phenylalanine onto said adsorbent to the substantial exclusion of the other feed components and recovering phenylalanine by desorbing with water. Phosphate salts can be recovered in the raffinate in the adsorption process by washing the adsorbent with acetic acid prior to use.

11 Claims, 4 Drawing Sheets

PROCESS FOR SEPARATING PHENYLALANINE FROM SALTS

BACKGROUND OF THE INVENTION

1. Field of the Invention

The field of art to which this invention pertains is the solid bed adsorptive separation of phenylalanine. More specifically, the invention relates to a process for separating and recovering L-phenylalanine (hereinafter "phenylalanine") from an aqueous solution of phenylalanine and salts employing a zeolitic adsorbent to selectively adsorb phenylalanine.

2. Description of the Prior Art

Phenylalanine is an essential amino acid and is used in the synthetic production of pharmaceuticals and more recently extensively in the production of "Aspartame", a non-nutritive sweetener sold under the trade name "Nutrasweet". There are several routes to the production of phenylalanine: the fermentation of sugar; the enzymatic reaction of cinnamic acid; hydantoin or other sources, e.g., phenylacetaldehyde. All of these routes produce phenylalanine, which is a zwitterion at a pH of 6.5, together with other reaction products, such as lactic acid, acetic acid, phenyllactic acid, cinnamic acid and hydrocinnamic acid, salts, such as KCl, $K_2SO_4$, $(NH_4)_2HPO_4$, etc., sugars, other amino acids and organic acids.

In U.S. Pat. No. 4,584,400, a process for separating L-phenylalanine from a fermentation broth by a chromatographic process with non-polar adsorbents, e.g., XAD-2 and XAD-4 is disclosed, where the predominant contaminant is L-tyrosine. However, enormous volumes of water, the desorbent, are required to desorb phenylalanine.

Phenylalanine has also been separated from cinnamic acid, as disclosed in U.S. Pat. No. 4,604,483, utilizing XAD-2, XAD-4, XAD-7 and XAD-8 in the presence of at least 0.1N solution of a salt, e.g., ammonium chloride. In this process, the selectivity of the adsorbent for the two components is reversed due to the greater salting-out effect of ammonium chloride on the cinnamic acid than on the phenylalanine. Thus, phenylalanine is eluted first with substantially no cinnamic acid. Applicant's invention does not rely on the salting-out effect on the selectivity.

U.S. Pat. No. 3,787,317 discloses the use of at least two different chromatographic materials, e.g., dextran-based molecular sieves, usually crosslinked, to separate mixtures which are stated to include phenylalanine.

A technical bulletin (undated) promulgated by Rohm and Haas Company discusses the use of Amberlite XAD-7 in several separations, viz. fatty acids from water or toluene; phenol or m-chlorophenol from water or toluene; proteins from aqueous fluids of biological origin. One of these general suggestions for separations is more specifically disclosed in U.S. Pat. No. 4,616,078, wherein proinsulin-like substances may be separated from impure mixtures obtained by recombinant DNA methodology by adsorption on Amberlite XAD-7 or XAD-8 and elution with acetone or acrylonitrile under specified conditions.

The use of crystalline aluminosilicates to perform a number of separations is well known in the separation art. Examples of such separations are the use of zeolites to separate normal paraffins from branched chain paraffins, (U.S. Pat. No. 2,985,589), faujasites to separate olefinic hydrocarbons from paraffinic hydrocarbons (U.S. Pat. No. 3,265,750), zeolites to separate specific monosaccharides or classes of monosaccharides from carbohydrate feed mixtures (U.S. Pat. No. 4,024,331), etc. To my knowledge, none have been proposed for this separation and recovery of phenylalanine.

While crystalline aluminosilicates or zeolites have been used in adsorption separations of various mixtures in the form of agglomerates having high physical strength and attrition resistance, to our knowledge an effective chromatographic process for purifying phenylalanine has not been found. Methods for forming the crystalline powders into agglomerates are also known and include the addition of an inorganic binder, generally a clay of the kaolin type comprising silicon dioxide and aluminum oxide, to a high purity zeolite powder in wet mixture. The blended clay zeolite mixture is extruded into cylindrical type pellets or formed into beads which are subsequently calcined in order to convert the clay to an amorphous binder of considerable mechanical strength. Water permeable organic polymers or silica are also amorphous and may also be used as binders which do not require calcining. Suitable water soluble organic binders include cellulose esters, such as cellulose acetate or cellulose acetate butyrate, or cellulose nitrate as disclosed in Kulprathipanja Patents 4,248,737 and 4,295,994. The method of incorporating the binder in the zeolite is disclosed in said patents, which disclosures are incorporated herein by reference.

None of the references disclose an effective and economic chromatographic process for separating phenylalanine from a fermentation broth and/or from salts dissolved therein.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principals are familiar, in sizes ranging from pilot plant scale (DeRosset U.S. Pat. No. 3,706,812) to commercial scale and flow rates from a few cc's per hour to many thousands of gallons per hour.

The functions and properties of adsorbents and desorbents in a chromatographic separation of liquid components are well known, but for reference thereto, Zinnen et al. U.S. Pat. No. 4,642,397 is incorporated herein.

SUMMARY OF THE INVENTION

The present invention is a process for separating phenylalanine from a feed comprising phenylalanine and salts, such as KCl and $K_2SO_4$, although fermentation feeds additionally comprising carbohydrates, amino acids and organic acids are contemplated. The process comprises contacting, at adsorption conditions, the feed mixture, while maintaining the pH of the feed mixture from 4 to 7, and selectively adsorbing phenylalanine onto an adsorbent, comprising a Y zeolite having exchangeable sites exchanged with sodium, potassium or calcium ions, or mixtures thereof, to the substantial exclusion of the other feed components and desorbing, under desorption conditions, the phenylalanine with a desorbent which comprises water.

It has now been discovered that Y-type zeolites exchanged with cations at cation exchange sites selected from the group Ca, Na, K, or mixtures thereof, are suitable adsorbents for the separation of phenylalanine from salts or from fermentation broths containing salts, provided certain conditions in the chromatographic separation process are maintained. Important parameters to be controlled in the process are pH of the feed mixture and temperature of the process. Previous attempts have shown the difficulty of separating the salts from phenylalanine.

DETAILED DESCRIPTION OF THE INVENTION

Figure 1:
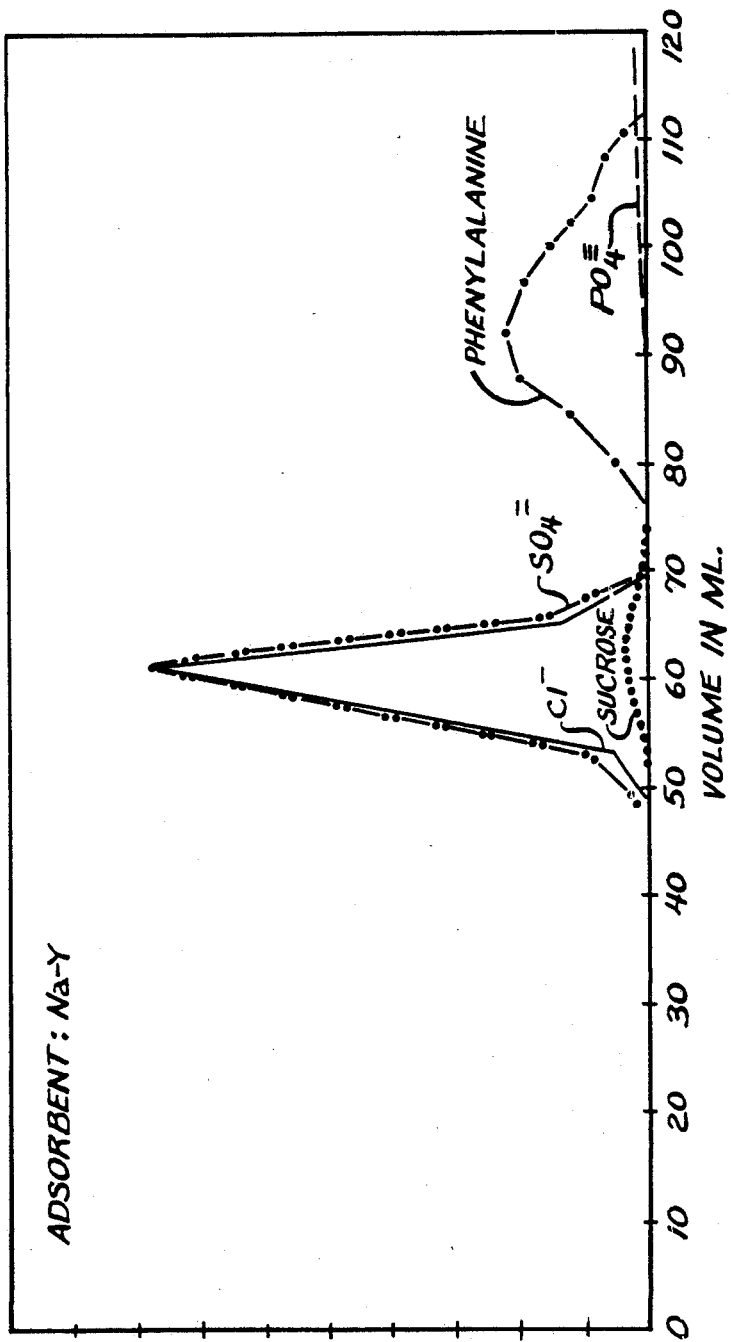

Adsorbents to be used in the process of this invention will comprise specific crystalline aluminosilicates or molecular sieves, namely Y zeolites. The Y zeolites have known cage structures in which the alumina and silica tetrahedra are intimately connected in an open three-dimensional network to form cage-like structures with window-like pores. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves".

In hydrated form, the Y zeolites used in the process of this invention have the structure described and defined in U.S. Pat. No. 3,130,007, incorporated herein by reference thereto. The Y zeolites in the hydrated or partially hydrated form can be represented in terms of moles of metal oxides as shown by Formula 1 below:

Formula 1

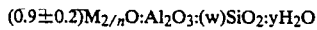

$(0.9 \pm 0.2)M_{2/n}O:Al_2O_3:(w)SiO_2:yH_2O$ where "M" is at least one cation having a valence not more than 3, "n" represents the valence of "M", "w" is a value from 3 to 6 and "y", representing the number of moles of water, is a value up to about 9 depending upon the identify of "M" and the degree of hydration of the crystal. The cation "M", as the zeolite is initially prepared, is usually predominately sodium, but for the purpose of this invention, the sodium may be replaced with calcium or potassium cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed and dried to a desired water content.

The adsorbent may be supported by an inorganic matrix material such as silica, titania, or alumina or mixtures thereof, or compounds, such as clays, which material is present in intimate mixture with the small particles of the zeolite material. Other binders such as water permeable organic polymers, e.g., cellulose acetate can also be used. This matrix material, or binder, typically in amounts ranging from 2-25 wt.%, aids in forming or agglomerating the particles and may be an adjunct of the manufacturing process for zeolite, (for example, intentionally incomplete purification of the zeolite during its manufacture) or it may be added to relatively pure zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh).

We have found that Y zeolites with sodium, potassium or calcium cations, or mixtures thereof and amorphous binders possess the selectivity and other necessary requirements for use in our process; however, a potassium-exchanged Y zeolite is particularly preferred, since the desorption is easier and faster and especially when the feed contains potassium salts.

As previously stated, there are several synthetic routes to the production of phenylalanine, but all result in a mixture of products from which phenylalanine must be separated. A suitable feed is the fermentation product of a carbohydrate source, such as sugar, which has been treated by ultrafiltration to remove certain of the impurities, such as residual cells, cell debris, etc. The feed contains salts, such as potassium chloride, potassium sulfate, $K_2SO_4$ and ammonium phosphate, $(NH4)_2HPO_4$, etc., and may also contain sugars, including glucose and maltose, organic acids, e.g., lactic, phenyllactic acids, cinnamic acid and other amino acids, such as alanine and lysine.

It is an important aspect of the process to maintain the pH in the range where the phenylalanine is present as a zwitterion and is hydrophobic. At this pH, most of the other components present in the feed will be hydrophilic and will elute at the void volume. The preferred pH will be in the range 4 to 7 with a pH of 6 being most preferred.

In the process of the present invention, a fermentation feed mixture containing phenylalanine, salts, carbohydrates, other amino acids and organic acids may be brought into contact with a Y zeolite, exchanged with sodium, potassium or calcium, or mixtures thereof, at the exchangeable sites, to thereby selectively adsorb the phenylalanine on said zeolite and thereafter the phenylalanine adsorbed onto the zeolite is desorbed by contacting the adsorbent with a desorbent comprising water. The separation process may be either batch or continuous and preferably is a fixed or moving adsorbent bed system, with the most preferred system being a countercurrent simulated moving bed system, such as described in the aforementioned Broughton U.S. Pat. No. 2,985,589, supra.

In this process, and particularly, the preferred continuous, simulated moving bed process, the desorbent must be selected to satisfy the following criteria: First, the desorbent material should displace an extract component from the adsorbent with reasonable mass flow rates without itself being so strongly adsorbed as to unduly prevent an extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will allow separation of at least a portion of desorbent material from feed components in the extract and raffinate streams by evaporation, using conventional apparatus, thereby permitting reuse of desorbent material in the process. Finally, desorbent materials should also be materials which are readily available and, therefore, reasonable in cost. However, a suitable desorbent or desorbents for a particular separation with a specific adsorbent are not always predictable. In the preferred isothermal, isobaric, liquid-phase operation of the process of my invention, I have found that desorbent material comprising water will result in selectivity for the adsorbed phenylalanine when used with the above discussed adsorbents. The combination of KY adsorbent and water was found to be most effective in separating phenylalanine from the salts in the feed.

Feed mixtures which can be utilized in the process of this invention will comprise a mixture of phenylalanine and at least one salt impurity, e.g., KCl, $(NH_4)_2HPO_4$, $K_2SO_4$, etc. Potential feed mixtures may also contain other products of the fermentation process, which normally will not be adsorbed. Mixtures may also contain significant quantities of other impurities. A typical feed mixture for this invention is a crystallization residue of the crude reaction mixture, e.g., the composition shown in Table 4. The invention is applicable to other feed mixtures, including crude reaction products or pretreated reaction products containing primarily phenylalanine and salts.

Phosphate ions in the feed can be troublesome, since they appear to be strongly adsorbed. Small amounts, however, are desorbed by water and constitute a contaminant in the phenylalanine product. While it would appear that phosphate ions do not reduce the capacity of the adsorbent for phenylalanine, phosphate ions would eventually reach a steady state with respect to the adsorbent sites, capable of adsorbing the phosphate ions and thereafter, excess phosphate ions in the feed would be eluted with the raffinate. This does not eliminate the problem of contamination, since some of the adsorbed phosphate ions would be desorbed in each cycle. A preferred method of dealing with this would be to remove the phosphates from the feed in a pretreatment, for example, by precipitating the phosphate ions as $Ca_3(PO_4)_2$ and removing the precipitate by filtration. The adsorbed phosphates can be desorbed, in a second desorption step with acetic acid or a dilute mineral acid, i.e., using dual desorbents, or as a swing bed operation by replacing the adsorbent beds from time to time with a fresh bed, removing the bed loaded with phosphate from service and washing with dilute sulfuric acid at a pH of about 3-4 to regenerate the bed.

In a most preferred embodiment of the invention, the adsorbent is washed with acetic acid, with a pH of 3 or greater, preferably about 4, prior to being used in the process. At too low a pH, i.e., around 2, the zeolitic framework can be damaged and this should be avoided. When the adsorbent has been pretreated in this way, phosphate ions are not adsorbed and are eluted at approximately the void volume with the salts. Phenylalanine can thus be recovered substantially free of phosphate contamination and it is not necessary to regenerate the adsorbent as above proposed or use dual desorbents. Liquid phase operation is used for this process.

Adsorption conditions will include a temperature range of from about 20° to about 200° C. with about 40° to about 80° C. being more preferred and a pressure sufficient to maintain liquid phase, ranging from about atmospheric to about 500 psig with from about atmospheric to about 25 psig being preferred. Desorption conditions will include the same range of temperatures and pressures as used for adsorption conditions.

At least a portion of the raffinate stream, which contains the salts and sugars, and preferably at least a portion of the extract stream containing the concentrated phenylalanine product, from the separation process, are passed to separation means, typically crystallizers or evaporators, where at least a portion of desorbent material is separated to produce a raffinate product and an extract product, respectively.

A dynamic testing apparatus is employed to test various adsorbents with a particular feed mixture and desorbent material to measure the adsorption characteristics of retention capacity and exchange rate. The apparatus consists of a vertical adsorbent chamber of approximately 100 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract or a raffinate component, the rate of desorption of an extract component from the adsorbent, the resolution between the components and selectivity for one component with respect to the other. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the otheer components.

EXAMPLE I

A pulse test, as described above, was run at 65° C. on 1 ml of a feed comprising 2% each of sucrose and phenylalanine and 0.5% each of pure components of K₂SO₄, KH₂PO₄ and KCl. The adsorbent was a cellulose acetate-bound Na-exchanged Y zeolite having particles sizes of 20 to 50 mesh. After the feed pulse was introduced, the desorbent water at a pH of 7 was introduced into the column flowing upwardly at a rate of 2 ml/min. The results are shown in the following Table 1.

TABLE 1

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| Sucrose | 62.5 | 1.2 | 10.7 | 2.7 | 2.2 |
| Cl⁻ | 60.3 | 0 | 7.1 | void | 2.5 |
| PO₄≡ | * | — | — | — | — |
| SO₄⁼ | 60.3 | 0 | 7.4 | void | 2.5 |
| Phenylalanine | 93.6 | 33.3 | 19.1 | reference | reference |

* [PO₄≡ions are strongly adsorbed and peak retention volume cannot be accurately determined.]

Resolution is a measure of the degree of separation of a two-component system, and can assist in quantifying the effectiveness of a particular combination of adsorbent, desorbent, conditions, etc. for a particular separation. Resolution for purposes of this application is defined as the distance between the two peak centers divided by the average width of the peaks at ½ the peak height as determined by the pulse tests described hereinafter. The equation for calculating resolution is thus:

$$R = \frac{L_2 - L_1}{1/2(W_1 + W_2)}$$

where $L_1$ and $L_2$ are the distance, in ml, respectively, from a reference point, e.g., zero to the centers of the peaks and $W_1$ and $W_2$ are the widths of the peaks at ½ the height of the peaks.

The examples shown below are intended to further illustrate the process of this invention without unduly limiting the scope and spirit of said process. The examples present test results for various adsorbent and desorbent materials when using the above dynamic testing apparatus.

The separation of phenylalanine is also shown graphically in FIG. 1. The figure and data in the table show that the phosphate ions are adsorbed and most of them remain on the adsorbent after desorption of the phenylalanine. Some of the PO₄≡ ions are desorbed and contaminate the phenylalanine. The PO₄≡ ions can be removed from the product by precipitation. The adsorbent will eventually be able to adsorb no more PO₄≡ ions, and they will be eluted with the salts, but the capacity of the adsorbent for phenylalanine does not appear to be reduced substantially. It may, nevertheless, be preferable to remove the PO₄≡ ions from the feed, for example, by pretreating with lime to precipitate Ca₃(PO₄)₂, which can be removed, e.g., by filtration. Alternatively, the PO₄≡ ions may be desorbed by using a second, stronger desorbent, e.g., acetic or and dilute mineral acid. Furthermore, as will be shown in Example IV, if the adsorbent is washed with acetic acid, PO₄≡ ions are eluted with the salts in the raffinate.

EXAMPLE II

Figure 2:
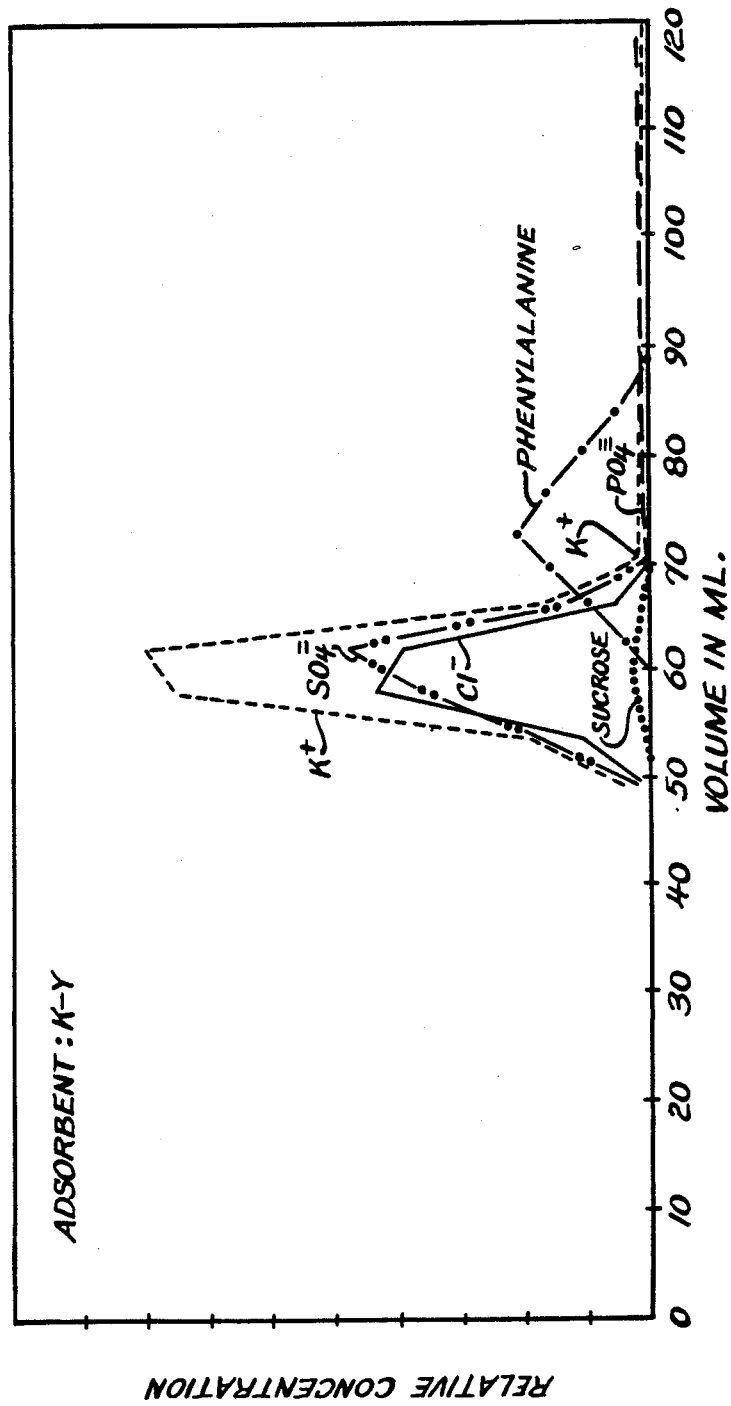

Another pulse test was run at 65° C. using the same feed as Example I, but with a cellulose acetate-bound potassium-exchanged Y zeolite. Again, water was the desorbent at a flow rate of 2 ml/min. The results are shown in FIG. 2 and the following Table 2.

TABLE 2

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| Sucrose | 60.8 | 0.9 | 11.2 | 15 | 1.03 |
| Cl⁻ | 59.7 | 0 | 9 | void | 1.1 |
| PO₄⁻³ | * | — | — | — | — |
| SO₄⁼ | 60 | 0.3 | 9.7 | 46 | 1.1 |
| K⁺ | 60 | 0.3 | 9.3 | 46 | 1.2 |
| Phenylalanine | 73.6 | 13.9 | 14 | reference | reference |

*See footnote to Table 1

EXAMPLE III

Figure 3:
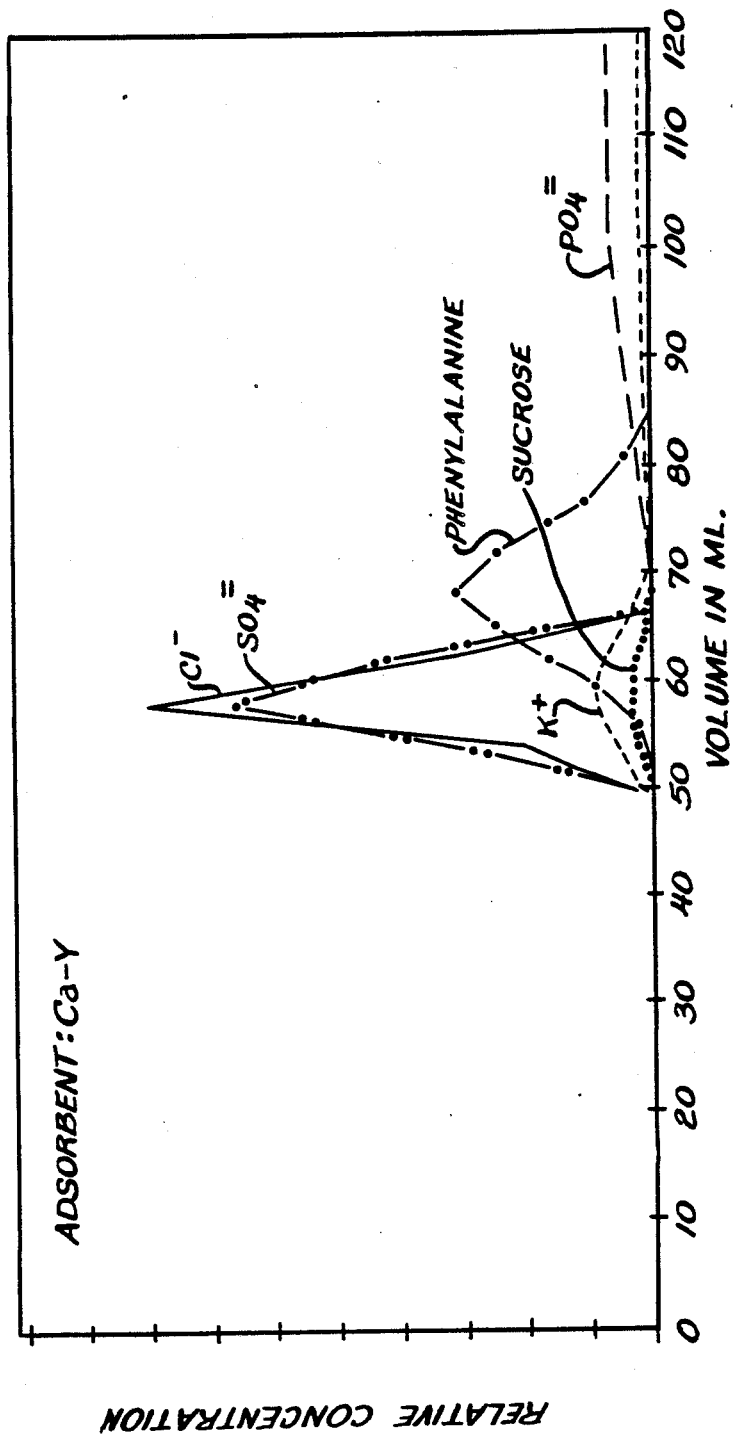

Another pulse test, run under the same conditions and with the same feed, desorbent, etc. as Example II, except that calcium-exchanged Y zeolite with a cellulose acetate polymeric binder was the adsorbent, gave the results shown in FIG. 3 and the following Table 3.

TABLE 3

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| Sucrose | 58.5 | 0.1 | 10.7 | 99 | 0.82 |
| Cl⁻ | 58.4 | 0 | 6.4 | void | 0.99 |
| PO₄≡ | * | — | — | — | — |
| SO₄⁼ | 58.6 | 0.2 | 8.7 | 50 | 0.89 |

TABLE 3-continued

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| $K^+$ | 58.4 | 0 | 11.3 | void | 0.81 |
| Phenylalanine | 68.3 | 9.9 | 13.1 | reference | reference |

*See footnote to Table 1

EXAMPLE IV

A fermentation broth was used as the feed mixture in a further pulse test, this time at a pH of 4.6 and having the composition in the following Table 4. The adsorbent, the potassium-exchanged Y zeolite of Example II, was washed, prior to use, with an aqueous solution of acetic acid at a pH of 4.

TABLE 4

| Composition | Wt. % |
|---|---|
| Phenylalanine | 3.0 |
| Sugar(glucose; $DP_2$, etc.) | 1.2 |
| Lactic Acid | 0.4 |
| Phenyllactic acid | 0.13 |
| $K^+$ | 0.247 |
| $NH_4^+$ | 0.35 |
| $PO_4^{-3}$ | 0.25 |
| $SO_4^{-2}$ | 0.98 |
| $Cl^-$ | 0.0015 |

Figure 4:
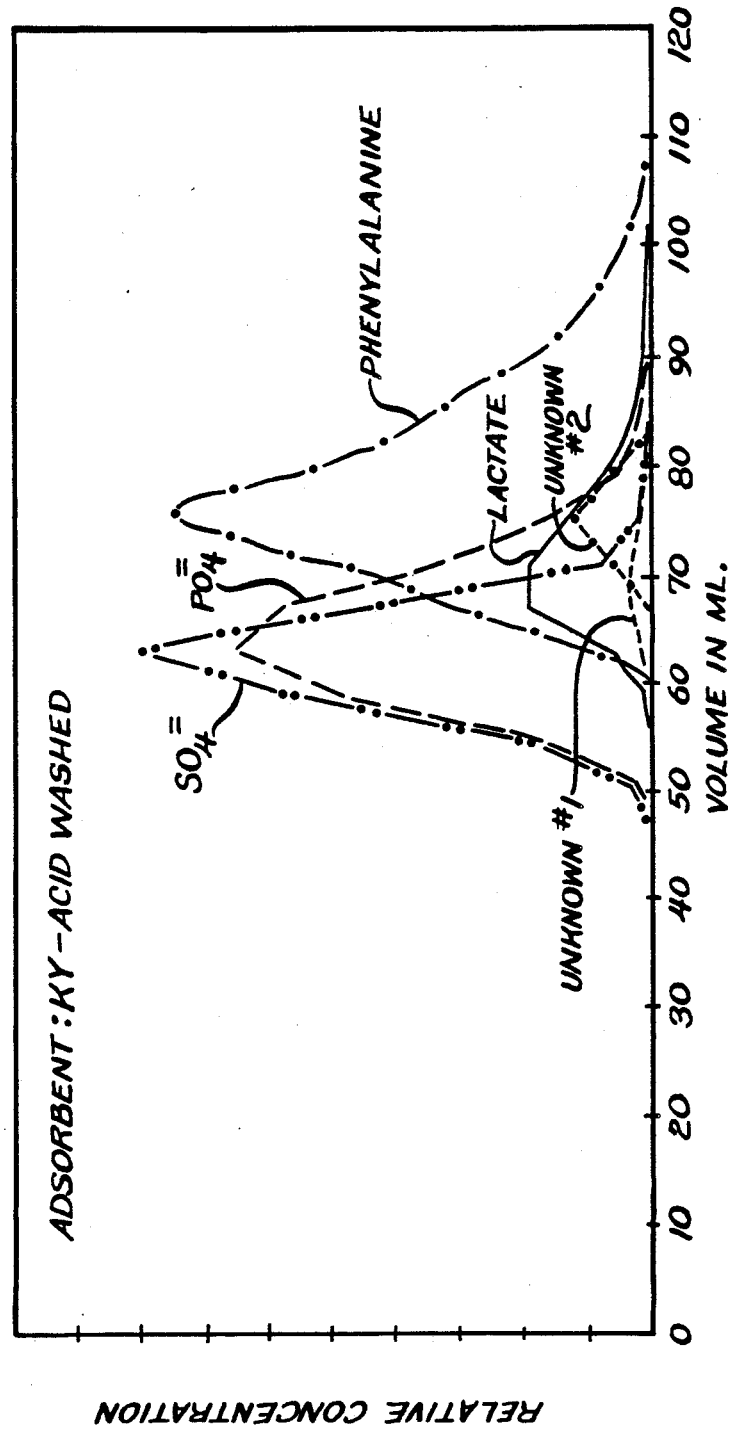

The results of the separation are shown in FIG. 4 and the following Table 5. It is particularly noted that the phosphate ions elute at the void volume.

TABLE 5

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| Sulfate ($SO_4^=$) | 62.1 | 0 | 10.4 | void | 1.10 |
| Phosphate ($PO_4^{-3}$) | 63.8 | 1.7 | 14.2 | 8.2 | 0.84 |
| Lactate | 70.5 | 8.4 | 13.2 | 1.65 | 0.39 |
| Unknown #1 | 69.4 | 7.3 | 11.9 | 1.90 | 0.48 |
| Unknown #2 | 75 | 12.9 | 7.7 | 1.08 | 0.09 |
| Phenylalanine | 76 | 13.9 | 14.8 | reference | reference |

What is claimed is:

1. A method for separating phenylalanine from a fermentation broth or an enzymatic reaction mixture comprising a solution of phenylalanine with inorganic salts and sugars comprising contacting said solution with an adsorbent comprising a Y zeolite exchanged at exchangeable cationic sites with sodium, potassium or calcium or mixtures thereof to effect the selective adsorption of said phenylalanine by said adsorbent and contacting said adsorbent with a desorbent at desorption conditions to remove said phenylalanine from said adsorbent and recovering said phenylalanine.

2. The method of claim 1 wherein said salts include sulfates, chlorides and phosphates.

3. The method of claim 2 wherein said adsorbent is prepared by washing with an acetic acid solution.

4. The method of claim 3 wherein the pH of said acetic acid is 4.

5. The method of claim 2 wherein said feed is pretreated to remove said phosphates.

6. The method of claim 1 wherein said desorbent is water.

7. The method of claim 1 wherein said desorption conditions include temperatures from 0° to 95° C.

8. The method of claim 1 where said solution pH is from 4 to 7.

9. The method of claim 1 wherein said exchange ion is calcium.

10. The method of claim 1 wherein said exchange ion is sodium.

11. The method of claim 1 wherein said exchange ion is a mixture of potassium with calcium or sodium.

* * * * *